US012699085B2

(12) United States Patent
Stanciu-Gregory et al.

(10) Patent No.: US 12,699,085 B2
(45) Date of Patent: Aug. 4, 2026

(54) MULTIFLUIDIC DEVICE AND PROCESSING SYSTEM FOR COLORIMETRIC MULTIPLEXED DETECTION OF A SUBSTANCE

(71) Applicant: Purdue Research Foundation, West Lafayette, IN (US)

(72) Inventors: Lia Antoaneta Stanciu-Gregory, West Lafayette, IN (US); Jan P. Allebach, West Lafayette, IN (US); George Tsu-Chih Chiu, West Lafayette, IN (US); Lixby S. Diaz, West Lafayette, IN (US); Min Zhao, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 1185 days.

(21) Appl. No.: 17/161,287

(22) Filed: Jan. 28, 2021

(65) Prior Publication Data
US 2021/0231646 A1 Jul. 29, 2021

Related U.S. Application Data

(60) Provisional application No. 62/966,836, filed on Jan. 28, 2020.

(51) Int. Cl.
*G01N 33/52* (2006.01)
*B41M 1/12* (2006.01)
(Continued)

(52) U.S. Cl.
CPC .............. *G01N 33/52* (2013.01); *B41M 1/12* (2013.01); *B41M 3/006* (2013.01); *G01N 21/79* (2013.01)

(58) Field of Classification Search
CPC ...... G01N 33/52; G01N 33/542; G01N 33/84; G01N 33/5308; G01N 21/78; G01N 21/79;
(Continued)

(56) References Cited

U.S. PATENT DOCUMENTS

| 8,377,710 | B2 * | 2/2013 | Whitesides | ....... | B01L 3/502761 |
| | | | | | 422/430 |
| 8,921,118 | B2 * | 12/2014 | Siegel | .............. | B01L 3/502707 |
| | | | | | 436/164 |

(Continued)

OTHER PUBLICATIONS

Maejima et al. RSC Advances, vol. 3, 2013, pp. 9258-9263.*
(Continued)

*Primary Examiner* — Maureen Wallenhorst
(74) *Attorney, Agent, or Firm* — Purdue Research Foundation

(57) ABSTRACT

A µPAD may include a paper-based substrate and a non-polar material printed on a surface of the substrate such that a portion the surface is exposed. The exposed portion may include a receiving area, a plurality of test areas, and a plurality of channels disposed between the receiving area and the test areas. The µPAD may further include colorimetric sensors respectively positioned in the test areas. The channel regions may be configured to receive an analyte solution from the receiving area and direct the analyte solution to the colorimetric sensors. A system may perform image processing on captured images of the µPAD to provide multiplexed analysis of analyte solutions applied to the µPAD.

15 Claims, 12 Drawing Sheets

(51) Int. Cl.
B41M 3/00 (2006.01)
G01N 21/79 (2006.01)

(58) Field of Classification Search
CPC ....... B41M 1/12; B41M 3/006; B01L 3/5027;
B01L 2400/0406; Y10T 436/25; Y10T
436/2575
USPC ....... 422/400, 408, 412, 417, 419, 420, 425,
422/69, 82.05, 501, 502, 504, 507;
436/73, 81, 164, 165, 169, 174, 180
See application file for complete search history.

(56) References Cited

U.S. PATENT DOCUMENTS

| | | | | |
|---|---|---|---|---|
| 9,791,434 | B2 * | 10/2017 | McCord ................. | G01N 33/52 |
| 2012/0238008 | A1 * | 9/2012 | Henry ................... | B01L 3/5023 |
| | | | | 435/288.7 |
| 2014/0178978 | A1 * | 6/2014 | Cate ....................... | G01N 21/78 |
| | | | | 422/402 |
| 2015/0132742 | A1 * | 5/2015 | Thuo ................. | B01L 3/502707 |
| | | | | 436/71 |
| 2016/0051980 | A1 * | 2/2016 | Hong ................... | G01N 33/558 |
| | | | | 506/39 |
| 2016/0139102 | A1 * | 5/2016 | McCord ................ | B01L 3/5023 |
| | | | | 435/287.7 |
| 2019/0111425 | A1 * | 4/2019 | Wronko ............ | B01L 3/502715 |
| 2019/0118175 | A1 * | 4/2019 | Kim ....................... | G01N 33/52 |

OTHER PUBLICATIONS

Somvanshi et al. Biosensors and Bioelectronics, vol. 207, Mar. 24, 2022, pp. 1-13.*
Ruivo et al. Analytical Biochemistry, vol. 538, Sep. 15, 2017, pp. 5-12.*
Chabaud et al. Forensic Chemistry, vol. 9, Apr. 3, 2018, pp. 35-41.*
Cai et al. AIP Advances, vol. 7, 2017, pp. 085214-1-085214-8.*
Xu, C. et al., Low-cost and rapid prototyping of microfluidic paper-based analytical devices by inkjet printing of permanent marker ink, RSC Advances, vol. 5, pp. 4770-4773. (2015).
Dungchai, W. et al., A low-cost, simple, and rapid fabrication method for paper-based microfluidics using wax screen-printing, Analyst, vol. 136, pp. 77-82. (2011).
Lamas-Ardisana, P.J. et al., Disposable electrochemical paper-based devices fully fabricated by screen-printing technique, Electrochemistry Communications, vol. 75, pp. 25-28. (2017); published online Nov. 26, 2016.
Yetisen, A.K. et al., A smartphone algorithm with inter-phone repeatability for the analysis of colorimetric tests, Sen-sors and Actuators B: Chemical, vol. 196, pp. 156-160. (2014); published online Feb. 12, 2014.
Brunelli, R., Template Matching Techniques in Computer Vision, Sep. 1, 2008; available online at https://www.researchgate.net/publication/252620698_Template_Matching_Techniques_in_Computer_Vision.
Hartigan, J. A. et al. , Algorithm AS 136: A K-Means Clustering Algorithm, Journal of the Royal Statistical Society. Series C (Applied Statistics), vol. 28, No. 1, pp. 100-108. (1979).
Otsu, N., Otsu, A Threshold Selection Method From Gray-Level Histograms, IEEE Transactions on Systems, Man, and Cybernetics, vol. SMC-9, No. 1, pp. 62-66. (1979).
Khan, W., Image Segmentation Techniques: A Survey, Journal of Image and Graphics, vol. 1, No. 4, pp. 166-170. (2013).
Chen, Q. et al., Filtering Airborne Laser Scanning Data With Morphological Methods, Photogrammetric Engineering & Remote Sensing, vol. 73, No. 2, pp. 175-182. (2007).
Dungchai, W. et al., Use of multiple colorimetric indicators for paper-based microfluidic devices, Analytica Chimica Acta 2010, vol. 674, pp. 227-233. (2010); published online Jun. 25, 2010.
Chun, H. J. et al., Paper-based Glucose Biosensing System Utilizing a Smartphone as a Signal Reader, BioChip J., vol. 8, No. 3, pp. 218-226 (2014); published online Sep. 20, 2014.

* cited by examiner

402

108

404

400
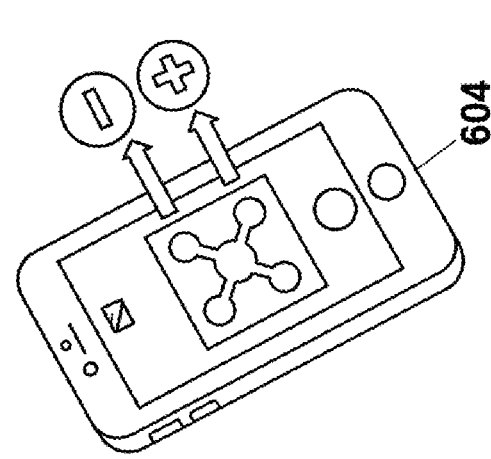
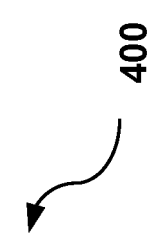
604
602
μPAD Framework
FIG. 6

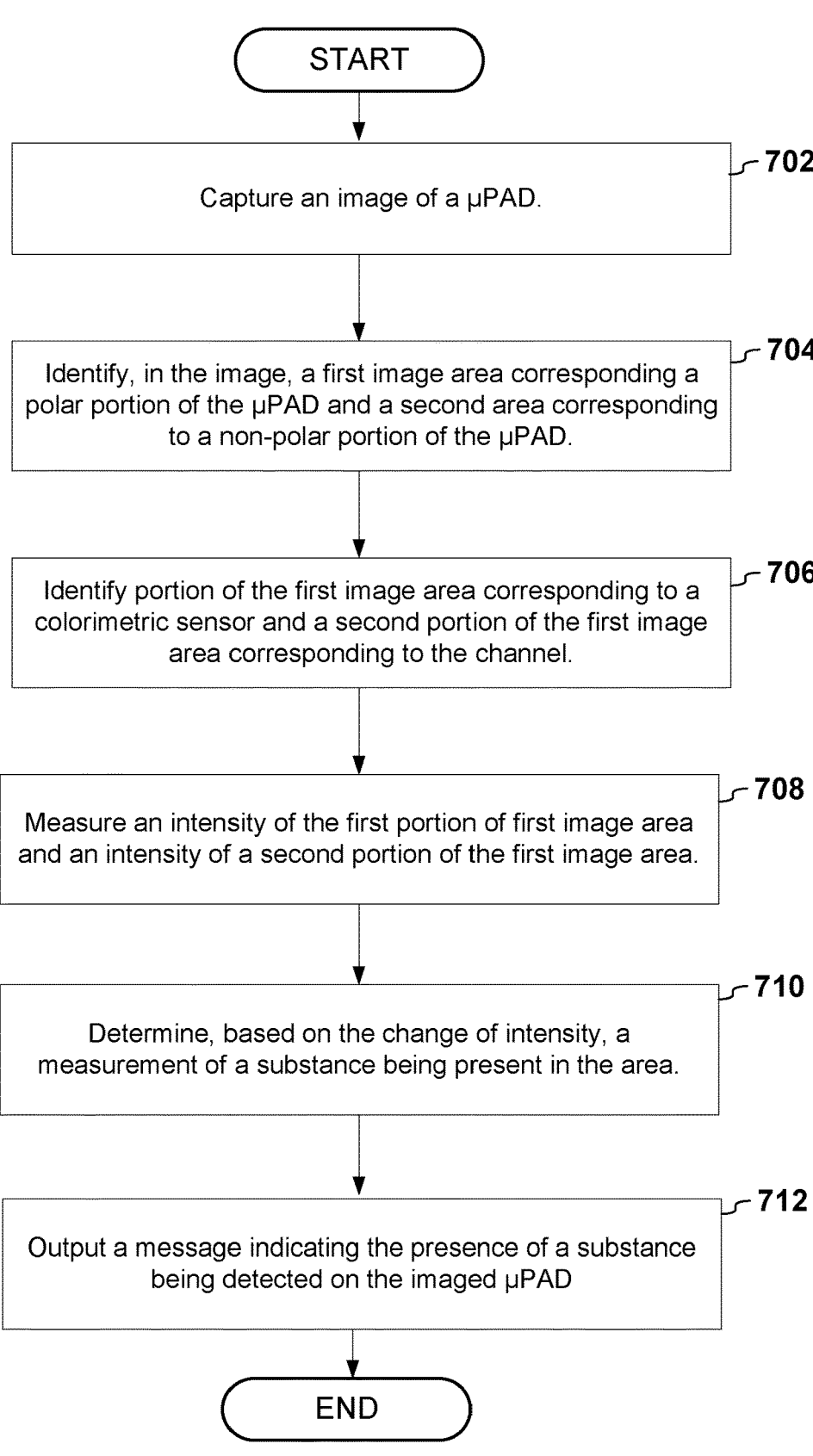

START

702 — Capture an image of a µPAD.

704 — Identify, in the image, a first image area corresponding a polar portion of the µPAD and a second area corresponding to a non-polar portion of the µPAD.

706 — Identify portion of the first image area corresponding to a colorimetric sensor and a second portion of the first image area corresponding to the channel.

708 — Measure an intensity of the first portion of first image area and an intensity of a second portion of the first image area.

710 — Determine, based on the change of intensity, a measurement of a substance being present in the area.

712 — Output a message indicating the presence of a substance being detected on the imaged µPAD

END

FIG. 7

MULTIFLUIDIC DEVICE AND PROCESSING SYSTEM FOR COLORIMETRIC MULTIPLEXED DETECTION OF A SUBSTANCE

CROSS REFERENCE TO RELATED APPLICATIONS

This application claims the benefit of U.S. Provisional Application No. 62/966,836 filed Jan. 28, 2020, the entirety of which is herein incorporated by reference.

GOVERNMENT LICENSE RIGHTS

This invention was made with government support under 59-8072-6-001 awarded by United States Department of Agriculture. The government has certain rights in the invention.

TECHNICAL FIELD

This disclosure relates to microfluidic devices and, in particular, image recognition and microfluidic devices.

BACKGROUND

The effective control and reduction of infectious diseases and environmental pollution caused by emerging pathogens and toxic chemical agents such as heavy metals, are major concerns worldwide. For example, Mercury and Arsenic have been recognized as chemical threats for human health because of their atmospheric transport, environmental persistence, capacity to bioaccumulate in living tissue and proven detrimental effects for human health at extremely low concentrations. In order to achieve these low limits of detection required by various governmental environmental agencies, a number of quantitative methods such as absorption/emission spectroscopy, inductively coupled plasma and cold vapor atomic fluorescence spectrometry have been traditionally used to effectively trace toxic metal ions in a variety of samples, showing an outstanding sensitivity and specificity. Despite their performance, these and other techniques involve expensive non-portable instrumentation, trained personnel for operation and sample preparation, preventing to achieve on-site, and real-time detection, and adding a layer of complexity when samples need to be transported to specialized laboratories, thus increasing testing time and the risk of sample contamination.

Unsurprisingly, paper-based assays have gained big attention due to their versatility, easy use, and low-cost. During the last few decades, a vast variety of paper-based biosensors have been successfully developed at the laboratory scale demonstrating an enormous potential looking for solving global issues such as food and environmental contamination. Despite the many advantages and opportunities brought by paper-based devices, the main drawback faced by these platforms is their limitation to deliver an analytical (quantitative) response.

Overall, the advancement of biosensors development at lab-scale is very promising. However, the fact that most of the emerging technologies won't reach the market is not yet an open topic of discussion within the field. There is evidence of a significant gap in-between the lab-bench technologies and manufacturing processes, where scaling-up challenges, economic viability, and inherent technology limitations have been ignored at early development stages, preventing technologies from ever been commercialized.

This restriction is mainly imposed by the cost-efficiency, stability of the biomolecules under harsh conditions, and high-scale reproducibility of the novel biosensing platforms.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

FIG. 6 illustrates a first example of a system;

FIG. 7 illustrates a flow diagram for logic for a system;

DETAILED DESCRIPTION

Figures 1A, 1B:
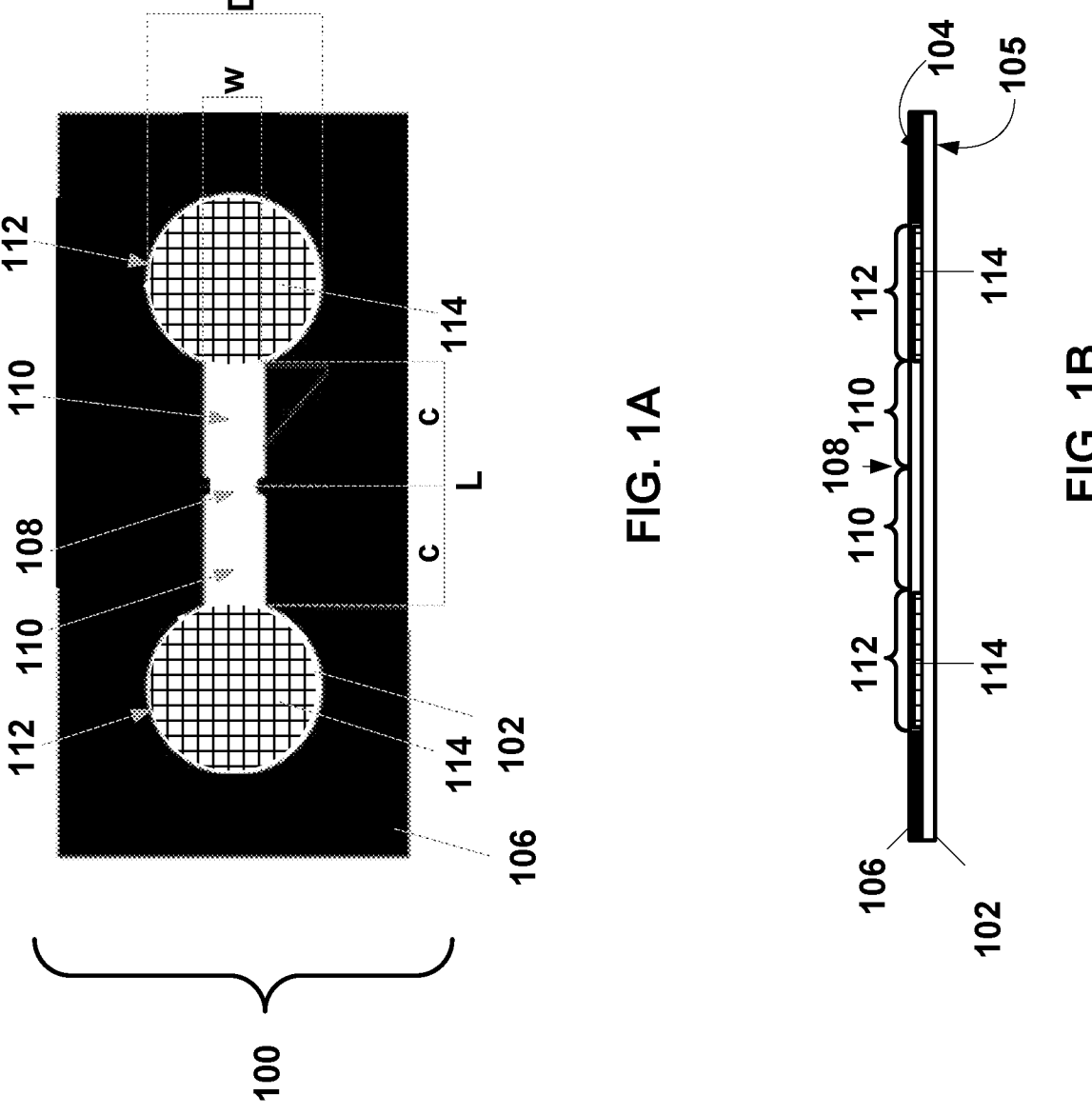
FIG. 1A-B illustrates a first example of a microfluidic paper-based analytical devices (μPAD)

A microfluidic paper-based analytical devices (μPAD) provide combine the advantages of paper strips with the functionality and utility of microfluidics. μPADS have the characteristic of controlling a fluid motion via capillary force through specially designed microfluidic channel patterns on cellulose paper. Cellulose papers with flexible porous fiber structure can wick liquids in small volumes without the need for external pumping equipment. μPADS provide various options for colorimetric analysis. Glucose detection still is a major driver of the biosensors field, and different approaches has been presented for its detection by using μPADS. However present approaches to response analysis systems lack multiple and multiplexed target detection, optimized testing area identification (area of interest segmentation) for provide controlled and consistent result analysis, and efficient manufacturing.

Accordingly, there is disclosed a μPAD and system and methods for colorimetric multiplexed detection of a target substance using the μPAD. The μPAD may include aptameric colorimetric sensors that provide multiple quantitative responses to the presence of targets in solutions. The solutions may deliver to the colorimetric sensors via multiple microfluidic channels where aptamers are immobilized on multiple pre-arranged testing areas. The microfluidic channels may be defined by a non-polar material applied and/or printed on a paper-based substrate, such as a μPAD. In various examples, the colorimetric sensors may be applied to and/or printed on to the paper-based substrate as well.

One example of a technical advancement described herein is that the μPAD enables multiplexed detection and quantification of tested analytes for an accurate and statistically significant analytical response. The μPAD may allow for the simultaneous data acquisition of multiple targets. Alternatively or in addition, the μPAD may minimize the number of times a test solution is applied to the μPAD by fluidly connecting multiple test areas to a receiving areas. This μPAD may be customized for heavy metal, aptamer based pathogen detection, and/or any analyte that might be detected via aptamer/DNA binding (whole cell, small molecules, ions or complementary DNA/RNA strands).

Another example of a technical advancement described herein is that the μPAD is fully integrated with image analysis. For example, the image analysis applies an optimized image segmentation process and color analysis derived from contrasts between the non-polar material, the paper-based substrate, and/or the colorimetric sensor response.

Another advancement herein is the μPAD may provide an on-site, low-cost, highly accurate and portable solution. The printable nature of the μPAD provides cheap and portable access to aptamer-based detection of analytical targets such as heavy metals, small molecules, bacteria or viruses. The multiplexed test sites enable accurate and statistically significant results. The contrasted patterns assist with on-site image analysis to identify response areas and quantify the response results. In some examples, a mobile phone, or other camera-based device local to the μPAD may capture an image of the μPAD and evaluate the image to provide a quantified result with minimal delay.

Additional benefits, efficiencies, and improvements over existing market solutions are made evident in the disclosure provided herein.

FIG. 1 illustrates a first example of a μPAD 100. FIG. 1A illustrates a top view of the μPAD 100 and FIG. 1B illustrates a cross section of the μPAD 100. The μPAD 100 may include a substrate 102. The substrate 102 may include a paper, (e.g. filter paper) that includes polar properties. For example, the substrate 102 may be hydrophilic and include a microfluidic paper or some other material that exhibits similar properties. The paper 102 may include a first side 104 and a second side (the second side not visible in FIG. 1).

The μPAD 100 may further include a non-polar material 106. The non-polar material 106 may include a chemical or material that, when applied to a surface of the substrate 102, prevents a solution from dissolving and/or prevents the solution from penetrating or diffusing. For example, the non-polar material 106 may include a hydrophobic material that acts as a barrier to a fluid. The non-polar material 106 may be printed on to the first side 104 of the substrate 102. In various examples, the non-polar material may include UV curable ink, wax, or some other suitable non-polar material that can be printed, sprayed, and/or commercially applied to the surface of the substrate 102. Alternatively or in addition, the non-polar material 106 may penetrate or be absorbed by the substrate 102 to imbue non-polar (i.e. hydrophobic) properties in a portion of the substrate 102 immediately below the location where the non-polar material 106 is applied.

The non-polar material 106 may cover and/or penetrate a portion of the surface of the substrate 102, leaving another portion exposed. For example, the non-polar material 106 may define an area where the surface of the substrate 102 is exposed. In other words, the substrate 102 may include an exposed surface where the non-polar material 106 is not covered by the non-polar material 106. The exposed surface may include a receiving area 108, one or more channel 110, and one or more test area 112.

Alternatively or in addition, the μPAD 100 may be created in a complement form. In other words, the substrate 102 may be a non-polar material, and an another material may be applied to the substrate 102 to define or change non-polar substrate to create the receiving area 108, channel(s) 110, and/or test areas 112. For example, the non-polar substrate may receive a material that changes the properties of the non-polar substrate to enable a capillary effect within the receiving area 108, channel(s) 110, and/or test areas 112. In other examples, a polar material may be printed onto the substrate to define the receiving area 108, channel(s) 110, and/or test areas 112.

The receiving area 108 may be an inlet for an analyte solution. For example, the receiving area may include a portion of the exposed surface that receives an analyte solution. The channel(s) 110 may include a portion of the exposed surface that extends away from the receiving area. The test areas 112 include a portion of the exposed surface where a solution is applied to a colorimetric sensor. For example, the test areas 112 may receive the solution from the channels 110. In some of the examples, the test areas 110 may be located at ends of the channels 110, respectively. As described herein, the terms "area" and "region" may be used interchangeably. An "area" and a "region" of the substrate, such as the test areas, channels, and/or receiving area, is a portion of a surface of the substrate that is at least partially bounded by the non-polar material or, in other words, not covered by the non-polar material.

Various parameters may be used to define the shape, layout, and measurement of the μPAD 100. For example, the test area 112 may have a width D. In the case of a circular test area, the width D would be a diameter. The channel 112 may have a width w. In addition, the channel may have a channel length c, which is defined as the distance between the receiving area 108 to the test area 112. The total channel length L is defined as the total channel length between two test areas (2c in the example illustrated in FIG. 1). In various examples, the test area 112 may have a wider width (D) than the width (w) of the channel 110 to accommodate a larger test area.

The μPAD may include one or more colorimetric sensor 114. A colorimetric sensor may include a material that changes color intensity in response to contact with a target substance. For example, the colorimetric sensors 114 may include an aptamer. An aptamer may include a short single stranded sequences of DNA or RNA highly specific for selected targets, and obtained through randomized selection by SELEX method. Aptamers possess interesting features such as their small size (increased surface coverage), flexible structure (enhanced penetration), and ability to recognize small molecules that fail in providing immune response; from the manufacturing point of view the most relevant facts are: they are inexpensive and chemically synthesized at high scales under controlled and standardized conditions. This coordination chemistry along with the evolving technologies for DNA chemical synthesis, and the introduction of nano-materials allowed the rapid development of a vast number of lab-scale biosensors. Alternatively or in addition, the colorimetric sensors 114 may include core polystyrene beads (430 nm) decorated with gold nanoparticles (20 nm) and DNA aptamers.

The colorimetric sensors 114 (and/or the test areas 112) may be spaced relative to the receiving area to provide even distribution of sample to achieve a homogenous flow velocity reaching simultaneous testing areas. For example, each of the channels 110 may have a length c such that the test areas 112 are equidistant from the receiving areas. The length c of the channel may be dependent on the aptamer composition and test requirements. Alternatively or in addition, different types of colorimetric sensors 114 may be applied to the test areas 112.

Fabrication of the μPAD may involve various steps to define the channel(s) and test areas. In various examples, inkjet printing, wax print and UV-curable ink screen printing may be to apply the non-polar material to the polar material.

Under the UV-curable inkjet methodology, nanoliter drops of UV curable ink may be printed onto the polar layer with a printer, such as a PipeJet Inkjet Printer. Thereafter, the printed ink may be cured with UV light to illuminate the printed UV-curable ink. The curing process imbues the ink with hydrophobic properties. Meanwhile, the unprinted regions (i.e. the exposed regions) of the polar layer retain their hydrophilic properties. In various experimentations, it was noticed that the actual channel width was smaller than the nominal width after the printing due to the long printing time and the fact that the solvents of the UV-curable ink spreads faster than the ink pigment, as illustrated in FIG. 1(a). In one example, the pigment defines a channel of width 4.5 mm, whereas the channel defined by the spread of the solvent is only 1.5 mm wide.

For wax screen printing, wax may be rubbed through a screen stencil with a squeegee to the polar layer. The printed paper is then heat-treated to allow the max to melt and spread vertically and laterally into the polar material to form the non-polar barriers. Finally, the printed paper is cooled to room temperature. In one example shows that the wax spreads unevenly after heating on a hot plate, therefore causing low-resolution printing, which may be unacceptable for some μPADs.

For UV-curable ink screen printing, a stencil may be used to perform the screen printing. In one example, a digital design may be printed on a transparent film with a laser printer. A screen is coated with an orange emulsion which is light sensitive. The printed pattern is pressed against the screen and exposed to UV-light to harden the emulsion. After washing the screen, a stencil of the digital design is created. Thereafter, a substrate is placed under the screen and affixed. Inks can be rubbed through the mesh of the white areas onto the substrate by a squeegee or other suitable device for mass production. Other manners of screen printing are possible. Experimental results of the UV-curable ink screen printing of the μPAD show that the diffusion of UV-curable ink is uniform.

Figure 2:
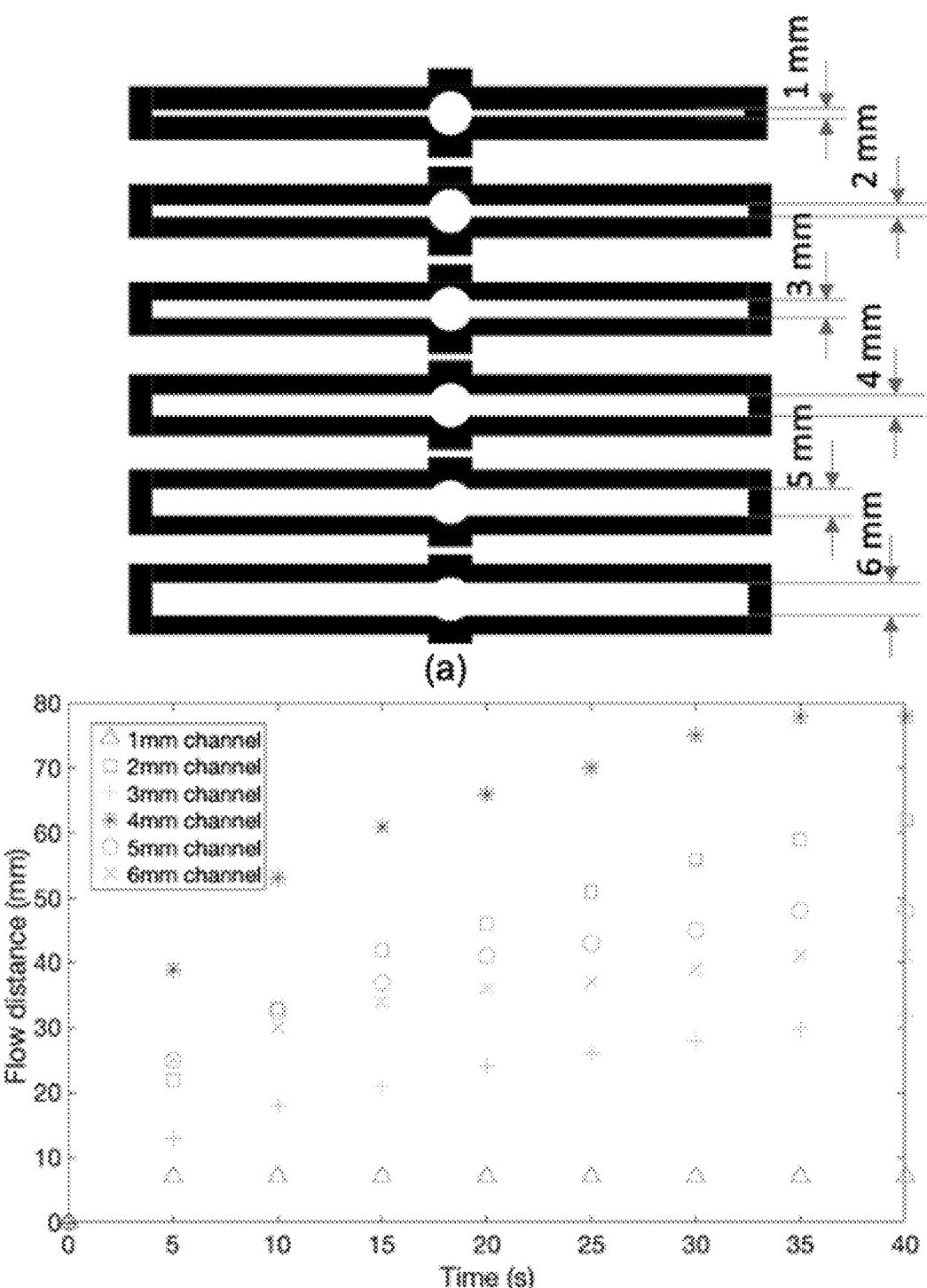
FIG. 2 illustrates an example relationship between channel width and the flow distance for the μPAD.

In various experimentation, the substrate 102 included Whatman chromatography filter paper (Grade No. 1, 20 cm width×20 cm length), stencils on aluminum frames with 230 polyester meshes (mesh opening 55 μm, Victory Factory, NY, USA), and UV curable inks (Ultra Switch UVSW180 and UVV6 Thinner, Maribu, Barcelona, Spain) are used to pattern the hydrophobic walls on the filter paper. The channel width was varied from 1 to 6 mm with an increment of 1 mm to observe the flow velocity and solution loss. FIG. 2 illustrates an example relationship between channel width w and the flow distance of 100 μl DI water which flows fastest when the channel width w equals 4 mm. Depending on the substrate and colorimetric sensor used, the width may be varied to achieve flow velocity/solution loss within design specifications.

Moreover, the total length (L) of the channels (or the combined channel lengths (c)) may be selected by pipetting aptamer-labels on two test zones and measuring the smallest channel length that prevents overlap after the label diffusion. To determine the optimal circle diameter of D (circle diameter), the diameter values may be varied between over a range (i.e. 8 mm to 12 mm) with regular increment (i.e. 2 mm). The value D may be chosen where the most visible color change is present.

Figure 3:
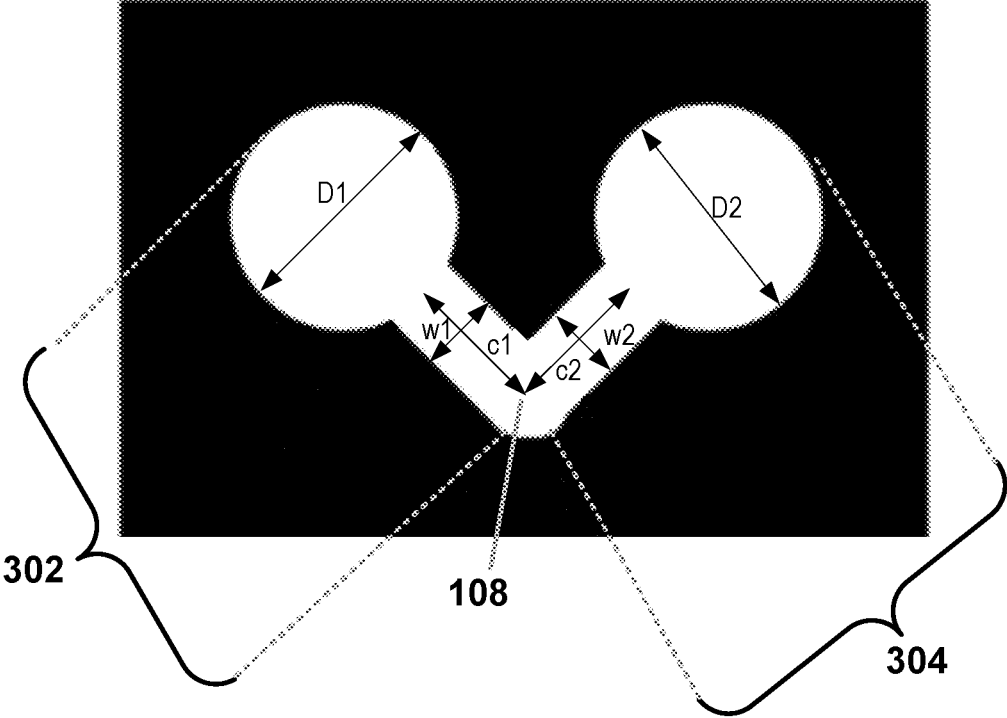
FIG. 3 illustrates a second example of a μPAD.

FIG. 3 illustrates a second example of the μPAD. The test areas may include the colorimetric sensors configured to detect the same or different targets. Depending on the colorimetric sensor used, the flow velocity through the test channels and/or the saturation time may be varied. Thus, the test area, and channel area may be varied.

By way of example, μPAD illustrated in FIG. 3 includes at least two test paths 302, 304. For example, the test paths may include corresponding test areas that are sized by diameters D1 and D2, respectively. The test paths may have corresponding channels may having lengths c1 and c2, respectively. The test paths may have corresponding channels with widths w1 and w2, respectively. The combinations (D1, c1, and w1) and (d2, c2, and w2) may be varied to ensure that the colorimetric sensors are ready for analysis at the same time after depositing the analyte solution in receiving area 108. In some examples, the channel lengths (c1, c2) may be equivalent to ensure equidistance between the receiving area and the testing areas. The equidistance may improve feature-based machine learning-based image recognition.

Figure 4:
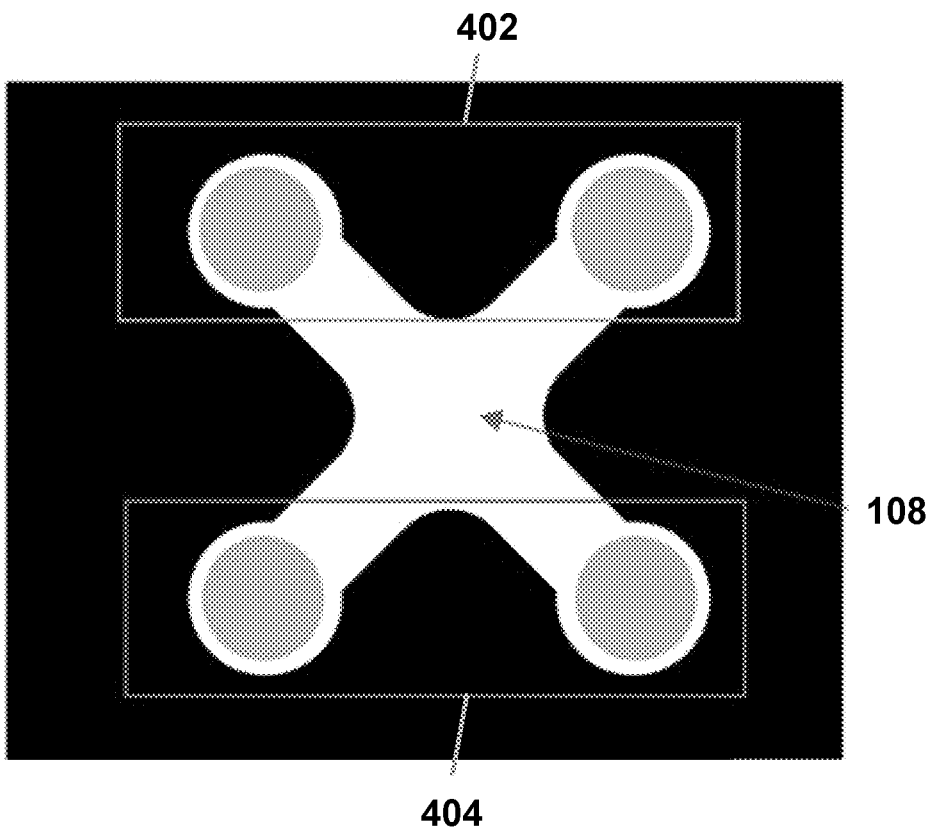
FIG. 4 illustrates a third example of a μPAD.

FIG. 4 illustrates a third example of the μPAD 100. The μPAD may include a first group of test zones 402 where a first type of colorimetric sensors are placed. The μPAD may have a second group of test zones 404 where a second type of colorimetric sensors are placed. The first type of colorimetric sensor may be configured to detect a different pathogen or heavy metal than the second type of colorimetric sensor. For example, aptamer-functionalized particles (ssDNA-PEI-Au-Ps) binding to $Hg^{2+}$ t may be inserted in to the first group of test zones. Aptamer-functionalized particles specific to $As^{3+}$ may be included on the second group of test zones.

Figure 5:
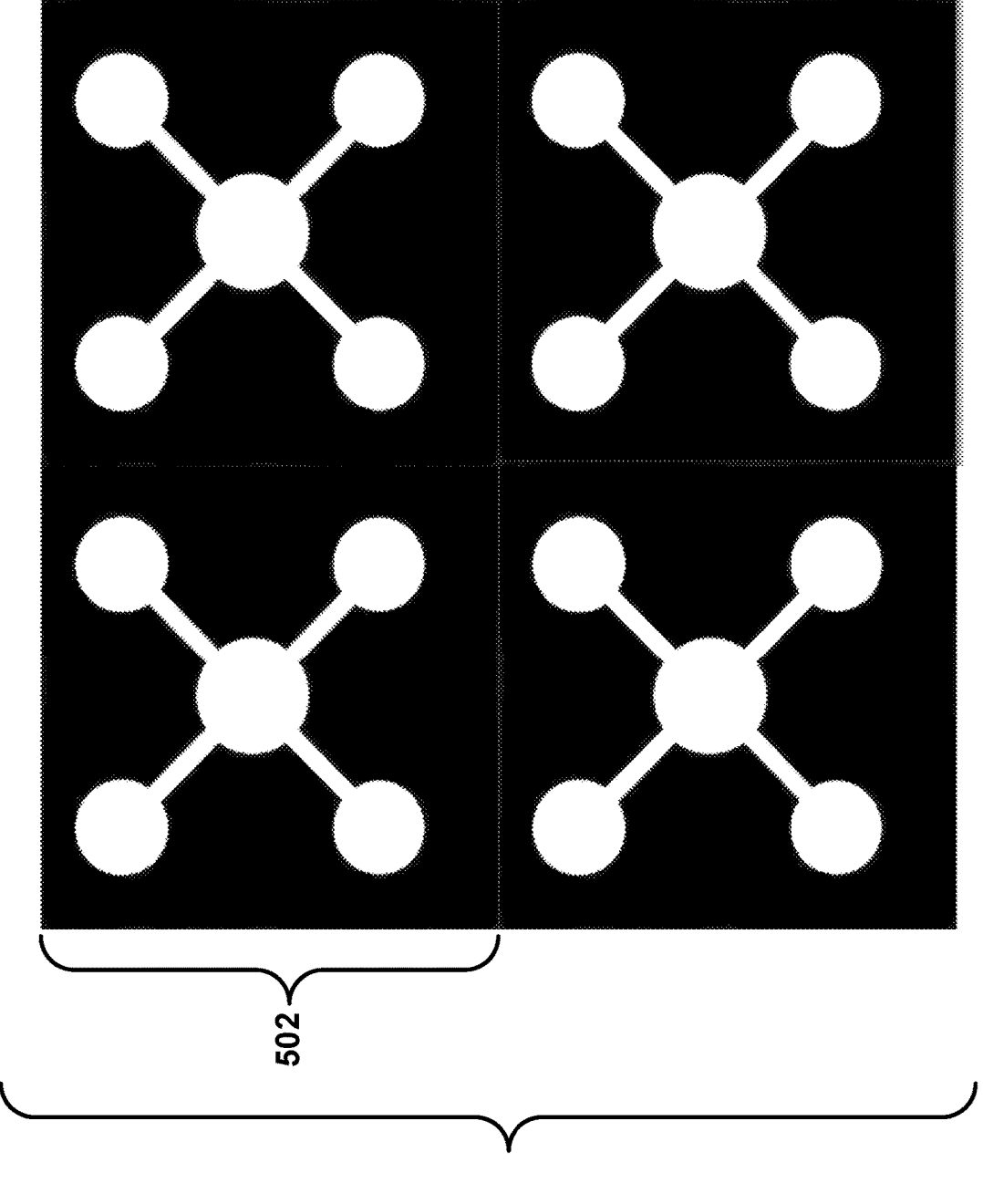
FIG. 5 illustrates a fifth example of a μPAD having multiple test sites.

FIG. 5 illustrates a fifth example of the μPAD with multiple test sites 502. A test site may include a portion of μPAD where the non-polar material 106 defines an exposed surface where a single receiving area is in fluid communicate with multiple test areas. The PAD may have multiple test sites 502 with corresponding receiving areas that are fluidly connected to sets of corresponding test areas. In some examples, each of the test sites included on the μPAD may have follow the same pattern such the same combination of channel width(s), channel length(s), and test area size(s) are used for each test site.

FIG. 6 illustrates a first example of a system 600. The system 600 may include a μPAD framework 602 and/or a capture device 604. In some examples, the μPAD framework 602 may be included in a server remote to the capture device 604. Alternatively, the test processing framework may be included in (or executed by) the capture device 604. The capture device 604 may include a camera. In some examples, the capture device 604 may be mobile device or computer system capable of network communication.

Prior to testing, functional colloidal suspension may be immobilized on the testing areas, serving as colorimetric label. When a sample is dropped in the receiving area, it flows evenly until reaching the testing areas where functionalized selective labels (i.e. colorimetric sensors) are deposited. Once the sample interacts with the labels there is a colorimetric response in presence of the targeted analyte. This signal (color shift from pink to deep purple) occurs as an effect of the interparticle distance change triggered by the DNA aptameric interaction with the analyte and is explained by the plasmonic properties of gold nanoparticles in the visible spectrum.

FIG. 7 illustrates a flow diagram for logic for the system 400. The capture device 502 may capture an image of a μPAD (702). Examples of the PAD 100 was previously described in reference to FIGS. 1-5. As previously discussed, the test site of the μPAD may include a non-polar portion and a polar portion. The polar portion may include a plurality of channels and a receiving region. The channels may respectively separate the test regions from the receiving region. The test site may further include colorimetric sensors respectively positioned on the receiving regions.

The µPAD framework 602 may identify, in the image, a first image area corresponding the polar portion and a second area corresponding to the non-polar portion (704). For example, the µPAD framework 602 may obtain grey scale images and then identify the polar and/or non-polar regions based on automatic image thresholding., which may binary or categorize the image data based on pixel intensities. A threshold intensity value may be determine using, for example, Otsu's method. In one example, the µPAD framework 602 may generate a histogram of a grayscale image data, µPAD framework 602 may apply an automatic imaging algorithm, such as Otsu's method, to find the optimal threshold intensity value that maximizes the between-class variance. Regions of the image data may be categories as either the polar portion or the non-polar portion based on the pixel intensity values being greater or less than the threshold intensity value.

The µPAD framework 602 may identify a first portion of the first image area corresponding to a colorimetric sensor and a second portion of the first image area corresponding to the channel (706). For example, the µPAD framework 602 may apply K-means clustering, or some other machine learning model, to identify the first and second portions (See FIG. 9 and related discussion).

The µPAD framework 602 may measure an intensity of the first portion of first image area and an intensity of a second portion of the first image area (708). The µPAD framework 602 may determine, based on a change of the intensity of the first portion of the first image area and the second portion of the first image area, a measurement of a substance being present in the area (710). As described below, correlations can be seen between the AE values and the increasing concentrations of the analytes. In some examples, the µPAD framework 602 may access model(s) that provide a concentration measurement based on the change of intensity and established correlation. Thus, one the chance of intensity is calculated, the system may access the model(s) and calculate an estimated concentration of a target substance based on the change of intensity. In some examples, a different model may be accessed for each analyte analyzed. Thus, for example, a first model may be accessed to calculate the concentration of a first target substance and a second model may be accessed to calculate the concentration of a second target substance.

The µPAD framework 602 may output a message indicating the presence of a substance being detected on the imaged µPAD (712). The message may be displayed on a graphical user interface. For example, the capture device 604, or some other device having a display, may display a graphic and/or text representative of the message. In some examples, the message may include the estimated concentration of the substance. Alternatively or in addition, the message may include indication along with a confidence score. In other examples, outputting the message may include storing the message in a database, outputting the message over a network, and/or otherwise making the message available to other electronic system(s) or device(s).

Figure 8:
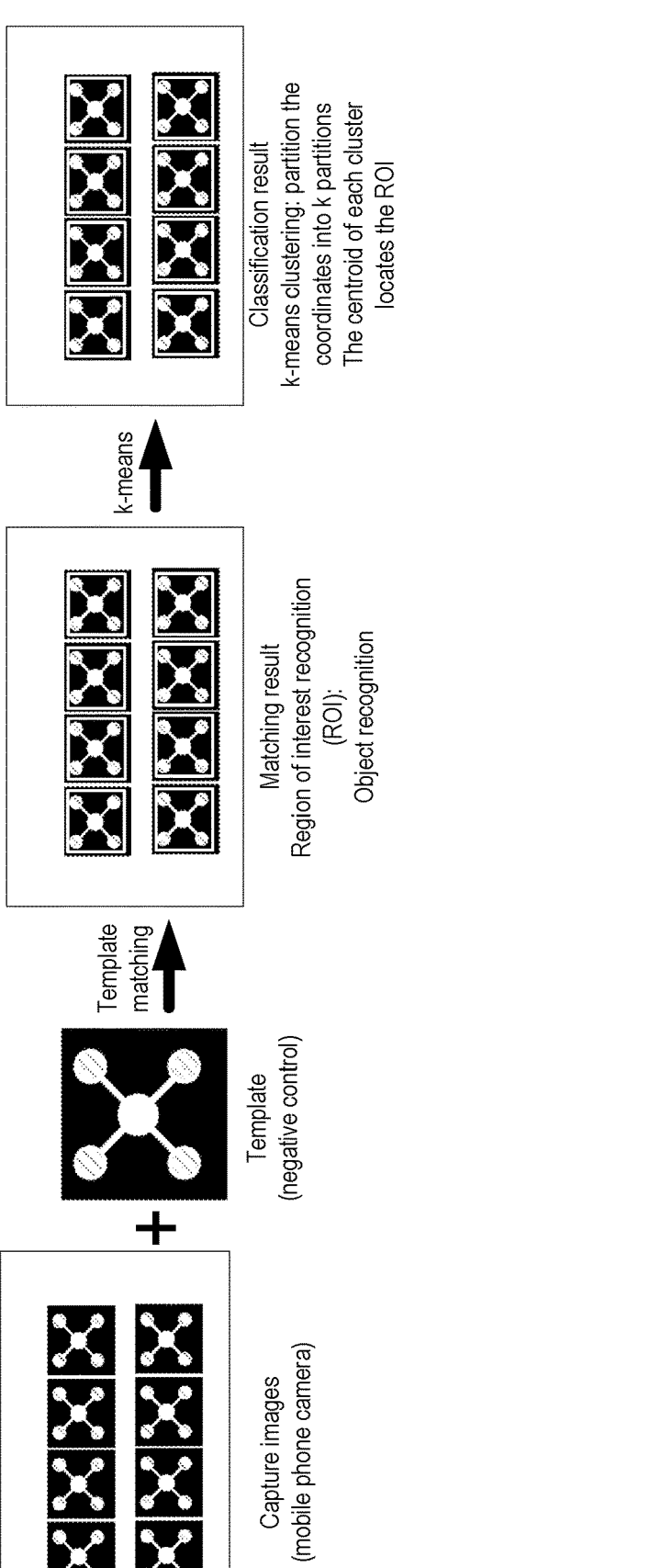
FIG. 8 illustrates example logic for processing an μPAD image with multiple test sites.

FIG. 8 illustrates example logic for processing a µPAD image with multiple test sites. The µPAD framework 602 may extract a region of interest (ROI). For example, the µPAD may apply template matching and/or k-means clustering or other relevant machine learning frameworks. For example, the machine learning framework may access a combination of a template (negative control: as-fabricated device tested with PBS) and an unsupervised clustering algorithm. Based on the color composition of any image (channels: Red, Green, and Blue), after each pixel is processed with the k-means clustering, centroids may correspond to the locations of multiple template images in a source image, locating the ROI. After a ROI is identified, the ROI may be further processed to obtain a quantified measurement of the results, as described in FIGS. 6 and 8.

Figure 9:
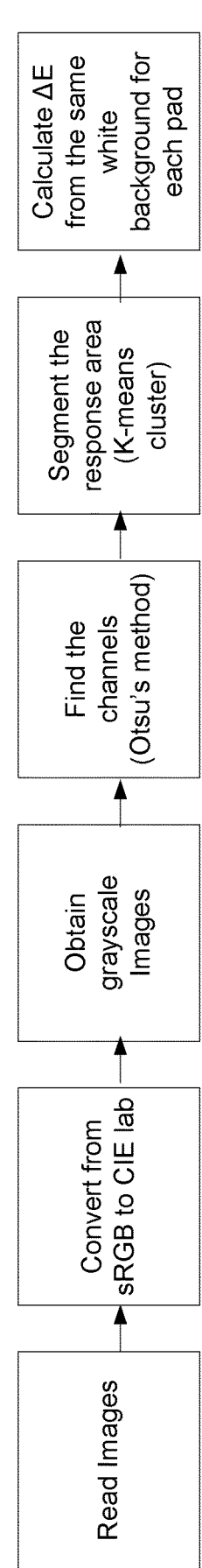
FIG. 9 an example logic for μPAD image processing with K-means clustering and Otsu's method.

FIG. 9 an example logic for µPAD image processing with K-means clustering and Otsu's method. The µPAD framework may execute image analysis based on original images, CIE lab conversion, Gray scale images, Channels identification (Otsu's method), segmentation (k-means clustering) and AE value calculation. For example, the original images are converted from sRGB to CIE lab to obtain grayscale images. Next, the channels of the µPAD are retrieved by Otsu's method, following with the application of the k-means clustering within the channel using the following feature selection: $[I, a, b, \Delta E, w \times i, w \times j]$ Where I, a, b are the pixel values in I, a, b channels.

$\Delta E$ is the grayscale values of each pixel.

i, j are coordinates of all pixels in row and column.

w is the weighted scale of coordinates (in this case w=0.05).

Number of clusters: K=5 (4 testing areas and the substrate 102 background)

Figure 10:
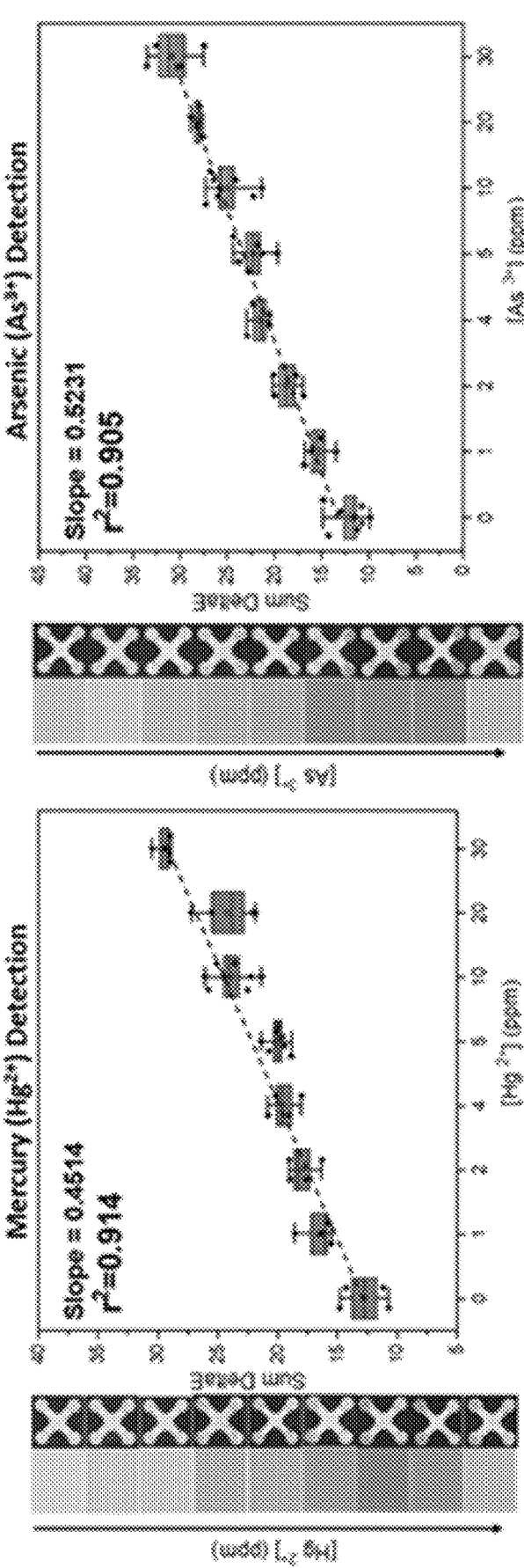
FIG. 10 illustrates an example of μPAD sensitivity.

In experiments, correlations were found between AE and increasing concentrations of analytes. FIG. 10 illustrates µPAD sensitivity. As illustrated in FIG. 10, a correlation was found between AE values vs. increasing concentrations of analytes. FIG. 10 shows the color evolution for each target under increasing concentrations along with the analytical response after image processing and analysis. According to the data collected, the variable $\Delta E$ and the metallic ions concentration were found to be strongly correlated ($p < 0.00001$). Where more than 90% of the colorimetric variation is explained by the increasing concentration of analytes. (Mercury $r2=0.914$ and Arsenic $r2=0.905$). The results presented in FIG. 8 show evidence of a linear correlation ([metallic ions] 0-30 ppm) with a limit of detection of 1 ppm.

Figure 11:
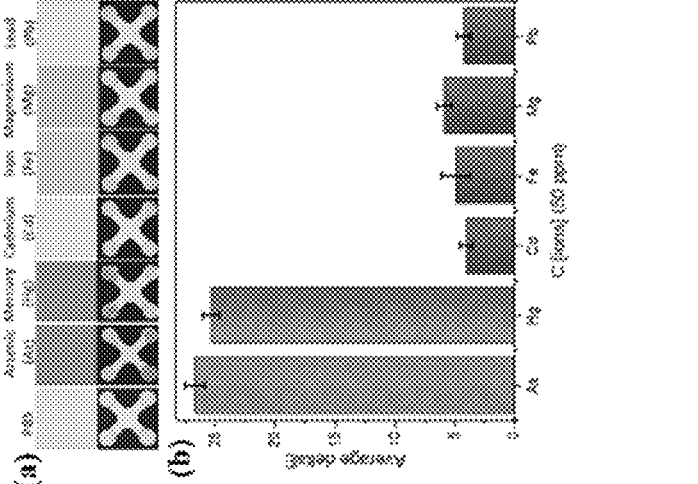
FIG. 11 illustrates an example of μPAD specificity.

Further testing was performed to assess the selectivity of the as-fabricated platform. It was tested with a pool of possible interferent ions and the same process was followed in order to acquire, segment, and analyze the images. Within the tested pool internal controls were included. As positive controls high concentrations of target (Mercury and Arsenic) were tested, in addition to a negative control (PBS). Using the signal analyzed from the negative control, the $\Delta E$ values were normalized. FIG. 11 illustrates the µPAD specificity (same concentrations for possible interferent ions tested). FIG. 11 includes real images and colorimetric response (a) and baseline normalized $\Delta E$ values (b). As illustrated in FIG. 11, $\Delta E$ values were calculated at high concentrations of Mercury & Arsenic along with interferent metallic ions (Cadmium, Iron, Magnesium and Lead) (50 ppm).

The logic illustrated in the flow diagrams and described herein may include additional, different, or fewer operations than illustrated. The operations illustrated may be performed in an order different than illustrated. The system may be implemented with additional, different, or fewer components than illustrated. Each component may include additional, different, or fewer components.

Figure 12:
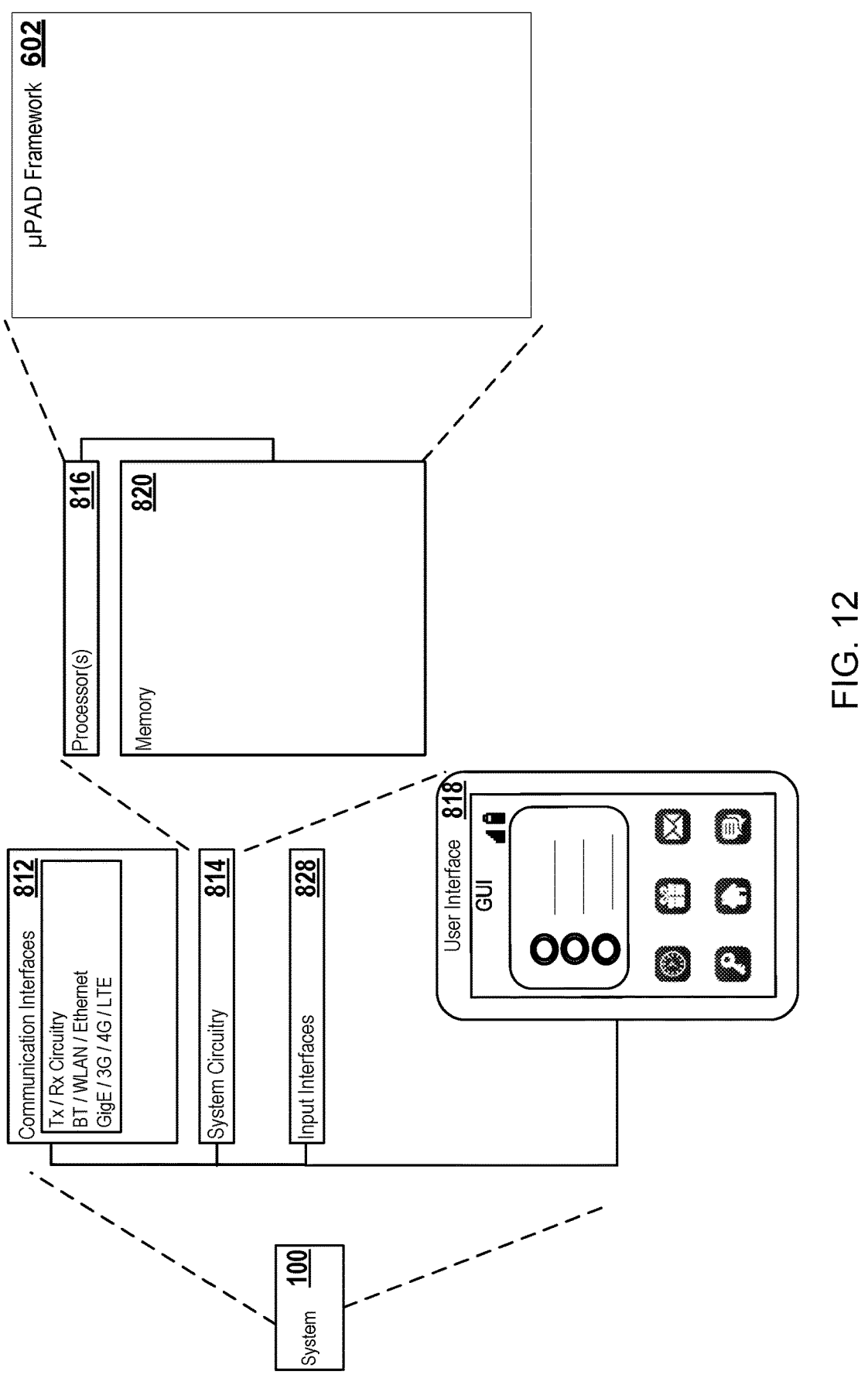
FIG. 12 illustrates a second example of a system.

FIG. 12 illustrates a second example of the system 400. The system 400 may include communication interfaces 812, input interfaces 828 and/or system circuitry 814. The system circuitry 814 may include a processor 816 or multiple processors. Alternatively or in addition, the system circuitry 814 may include memory 820.

The processor 816 may be in communication with the memory 820. In some examples, the processor 816 may also be in communication with additional elements, such as the communication interfaces 812, the input interfaces 828, and/or the user interface 818. Examples of the processor 816 may include a general processor, a central processing unit, logical CPUs/arrays, a microcontroller, a server, an application specific integrated circuit (ASIC), a digital signal processor, a field programmable gate array (FPGA), and/or a digital circuit, analog circuit, or some combination thereof.

The processor 816 may be one or more devices operable to execute logic. The logic may include computer executable instructions or computer code stored in the memory 820 or in other memory that when executed by the processor 816, cause the processor 816 to perform the operations the μPAD framework and/or the system 400. The computer code may include instructions executable with the processor 816.

The memory 820 may be any device for storing and retrieving data or any combination thereof. The memory 820 may include non-volatile and/or volatile memory, such as a random access memory (RAM), a read-only memory (ROM), an erasable programmable read-only memory (EPROM), or flash memory. Alternatively or in addition, the memory 820 may include an optical, magnetic (hard-drive), solid-state drive or any other form of data storage device. The memory 820 may include at least one of the PAD framework and/or the system 400. Alternatively or in addition, the memory may include any other component or sub-component of the system 400 described herein.

The user interface 818 may include any interface for displaying graphical information. The system circuitry 814 and/or the communications interface(s) 812 may communicate signals or commands to the user interface 818 that cause the user interface to display graphical information. Alternatively or in addition, the user interface 818 may be remote to the system 400 and the system circuitry 814 and/or communication interface(s) may communicate instructions, such as HTML, to the user interface to cause the user interface to display, compile, and/or render information content. In some examples, the content displayed by the user interface 818 may be interactive or responsive to user input. For example, the user interface 818 may communicate signals, messages, and/or information back to the communications interface 812 or system circuitry 814.

The system 400 may be implemented in many different ways. In some examples, the system 400 may be implemented with one or more logical components. For example, the logical components of the system 400 may be hardware or a combination of hardware and software. The logical components may include the μPAD framework and/or or any component or subcomponent of the system 400. In some examples, each logic component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each component may include memory hardware, such as a portion of the memory 820, for example, that comprises instructions executable with the processor 816 or other processor to implement one or more of the features of the logical components. When any one of the logical components includes the portion of the memory that comprises instructions executable with the processor 816, the component may or may not include the processor 816. In some examples, each logical component may just be the portion of the memory 820 or other physical memory that comprises instructions executable with the processor 816, or other processor(s), to implement the features of the corresponding component without the component including any other hardware. Because each component includes at least some hardware even when the included hardware comprises software, each component may be interchangeably referred to as a hardware component.

Some features are shown stored in a computer readable storage medium (for example, as logic implemented as computer executable instructions or as data structures in memory). All or part of the system and its logic and data structures may be stored on, distributed across, or read from one or more types of computer readable storage media. Examples of the computer readable storage medium may include a hard disk, a floppy disk, a CD-ROM, a flash drive, a cache, volatile memory, non-volatile memory, RAM, flash memory, or any other type of computer readable storage medium or storage media. The computer readable storage medium may include any type of non-transitory computer readable medium, such as a CD-ROM, a volatile memory, a non-volatile memory, ROM, RAM, or any other suitable storage device.

The processing capability of the system may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL).

All of the discussion, regardless of the particular implementation described, is illustrative in nature, rather than limiting. For example, although selected aspects, features, or components of the implementations are depicted as being stored in memory(s), all or part of the system or systems may be stored on, distributed across, or read from other computer readable storage media, for example, secondary storage devices such as hard disks, flash memory drives, floppy disks, and CD-ROMs. Moreover, the various logical units, circuitry and screen display functionality is but one example of such functionality and any other configurations encompassing similar functionality are possible.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one example, the instructions are stored on a removable media device for reading by local or remote systems. In other examples, the logic or instructions are stored in a remote location for transfer through a computer network or over telephone lines. In yet other examples, the logic or instructions are stored within a given computer and/or central processing unit ("CPU").

Furthermore, although specific components are described above, methods, systems, and articles of manufacture described herein may include additional, fewer, or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same apparatus executing a same program or different programs. The components may be resident on separate hardware, such as separate removable circuit boards, or share common hardware, such as a same memory and processor for implementing instructions from the memory. Programs may be parts of a single program, separate programs, or distributed across several memories and processors.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations.

What is claimed is:

1. A microfluidic paper-based analytical device (μPAD) comprising:
   a paper-based substrate
   a non-polar material printed on a surface of the substrate such that a portion the surface is exposed, the exposed portion comprising a receiving area, a plurality of test areas, and a plurality of channels disposed between the receiving area and the test areas; and a plurality of colorimetric sensors respectively positioned in the test areas, the colorimetric sensors having respective aptamers requiring different saturation times before they are ready for analysis, wherein the channels are configured to receive an analyte solution from the receiving area and direct the analyte solution to the colorimetric sensors,
wherein the receiving area is centrally positioned on the substrate and all of the test areas on the substrate are equidistant from the central receiving area to provide a consistent location for analysis of the test areas,
wherein the widths of each of the channels are not the same and are sized to control a flow velocity of the analyte solution to each test area, such that the analyte solution arrives at each of the respective aptamers at times coordinated with the required saturation time of that aptamer, thereby ensuring that all test areas, despite having the aptamers requiring the different saturation times, reach readiness for analysis simultaneously.

2. The μPAD of claim 1, wherein the non-polar material comprises UV curable ink.

3. The μPAD of claim 1, wherein the aptamers are configured to change color when in contact with a target substance included in the analyte solution.

4. The μPAD of claim 3, wherein the aptamers comprise gold nano-particles.

5. The μPAD of claim 3, wherein the aptamers are configured to change color in response to a heavy metal.

6. The μPAD of claim 5, wherein the heavy metal comprises Arsenic Mercury, or a combination thereof.

7. The μPAD of claim 1, wherein a pixel intensity of the non-polar material is different than a pixel intensity of the substrate.

8. The μPAD of claim 1, wherein the colorimetric sensors comprise a first and second colorimetric sensor, wherein the first colorimetric sensor comprises a first aptamer and the second colorimetric sensor comprises a second aptamer, wherein the first aptamer is configured to detect a different substance than the second aptamer.

9. A method of making a microfluidic paper-based analytical device (μPAD), the method comprising:
   printing a non-polar material on a paper substrate in a pattern that leaves a portion of the paper substrate exposed, the exposed portion comprising a receiving area centrally positioned on the substrate, a plurality of test areas, and a plurality of equidistant channels having different widths, the channels extending from the receiving area to the test areas, respectively; and
   depositing a plurality of colorimetric sensors on the substrate in the test areas, respectively the colorimetric sensors having aptamers requiring different saturation times before they are ready for analysis,
   wherein the differing widths of the channels control flow velocity of an analyte solution so as to coordinate delivery of the analyte solution to the aptamers at times coordinated with the required saturation times of the aptamers, thereby compensating for the different saturation times and providing substantially simultaneous readiness for the analysis of the colorimetric sensors.

10. The method of claim 9, wherein the non-polar material comprises UV curable ink, wax, or a combination thereof.

11. The method of claim 9, wherein the printing comprising screen printing or inkjet printing.

12. The method of claim 9, wherein the aptamers are configured to change color when in contact with a target substance included in the analyte solution.

US 12,699,085 B2

13

13. The method of claim 12, wherein the aptamers comprise gold nano-particles.

14. The method of claim 12, wherein the aptamers are configured to change color in response to a heavy metal.

15. The method of claim 9, wherein depositing the colorimetric sensors further comprises:

depositing a first colorimetric sensor in a first test area and a second colorimetric sensor in a second area, wherein the first colorimetric sensor comprises a first aptamer and the second colorimetric sensor comprises a second aptamer, wherein the first aptamer is configured to detect a different substance than the second aptamer.

\* \* \* \* \*

14